(12) United States Patent
Lee (10) Patent No.: US 8,983,569 B2
(45) Date of Patent: Mar. 17, 2015

(54) COMFORTABLY SECURING PHYSIOLOGICAL SENSORS ONTO A PERSON DURING SLEEP

(71) Applicant: Zinus, Inc., Hayward, CA (US)

(72) Inventor: Youn Jae Lee, Pleasanton, CA (US)

(73) Assignee: Zinus, Inc., San Leonardo, CA (US)

( * ) Notice: Subject to any disclaimer, the term of this patent is extended or adjusted under 35 U.S.C. 154(b) by 0 days.

(21) Appl. No.: 13/924,562

(22) Filed: Jun. 22, 2013

(65) Prior Publication Data

US 2014/0378808 A1    Dec. 25, 2014

(51) Int. Cl.
*A61B 5/0478*    (2006.01)
*A61B 5/00*    (2006.01)
*A61B 3/113*    (2006.01)

(52) U.S. Cl.
CPC ............. *A61B 5/6803* (2013.01); *A61B 5/4812* (2013.01); *A61B 5/0478* (2013.01); *A61B 3/113* (2013.01)
USPC ............................ 600/383; 600/544; 600/545

(58) Field of Classification Search
CPC .. A61B 5/0478; A61B 5/6803; A61B 5/4812; A61B 3/113

USPC .......................................... 600/383, 544, 545
See application file for complete search history.

(56) References Cited

U.S. PATENT DOCUMENTS

| 8,784,293 B2* | 7/2014 | Berka et al. | 600/26 |
| 2007/0249952 A1* | 10/2007 | Rubin et al. | 600/544 |
| 2013/0060097 A1* | 3/2013 | Rubin | 600/301 |

\* cited by examiner

*Primary Examiner* — Lee S Cohen
(74) *Attorney, Agent, or Firm* — Imperium Patent Works; Amir V. Adibi

(57) ABSTRACT

A physiological sensor apparatus comprises a physiological sensor, a headband and an eye mask. In one example, the physiological sensor includes a plurality of electroencephalography (EEG) electrodes that are used to sense a signal indicative of a sleep stage (e.g., REM sleep or non-REM sleep) of a user. Each end of the headband attaches to respective ends of the sensor and eye mask such that when the sensor is disposed on the forehead of the user, the eye mask shields the eyes of the user from visible light. The diameter of the headband is adjustable by the user to secure the sensor to the forehead of the user. The sensor accurately determines the sleep stages of the user over a period of sleep of the user because the adjustable headband and eye mask prevent the electrodes from being displaced from the forehead of the user during the period of sleep.

20 Claims, 14 Drawing Sheets

FRONT VIEW
(FIRST EMBODIMENT)

FRONT VIEW
(PRIOR ART)
FIG. 1

BACK VIEW
(PRIOR ART)
FIG. 2

(PRIOR ART)
FIG. 3

FRONT VIEW
(FIRST EMBODIMENT)

FIG. 4

BACK VIEW
FIG. 5

SIDE VIEW
FIG. 6

FIG. 7

ATTACHING SENSOR TO FOREHEAD
USING HEADBAND WITH EYE MASK ATTACHMENT

FIG. 8

HEADBAND AND EYE MASK SECURE
SENSORS TO FOREHEAD DURING SLEEP

FIG. 9

HEADBAND AND EYE MASK WORN UPSIDE DOWN
SECURE SENSORS TO FOREHEAD DURING SLEEP

FRONT VIEW
FIG. 12

ATTACHING SENSOR TO FOREHEAD
USING HEAD CAP

FIG. 13

HEAD CAP SECURES SENSORS TO
FOREHEAD DURING SLEEP

FIG. 14

FIG. 15

COMFORTABLY SECURING PHYSIOLOGICAL SENSORS ONTO A PERSON DURING SLEEP

TECHNICAL FIELD

The described embodiments relate to physiological sensors, and more particularly, to securing physiological sensors onto a user.

BACKGROUND INFORMATION

Sleep significantly impacts quality of life of an individual. The human sleep cycle generally conforms to a circadian rhythm that is regulated by a biological clock. Regular periods of sleep enable the body and mind to rejuvenate and rebuild. Normal sleep is characterized by a general decrease in metabolic rate, body temperature, blood pressure, breathing rate, heart rate, and other physiological functions. Normally a person alternates between a rapid eye movement (REM) sleep stage and a non-REM (NREM) sleep stage in approximately 90 minute cycles throughout a time period of sleep. A typical eight hour period of sleep may comprise a five-step sleep cycle identifiable through electroencephalogram (EEG) brain wave activity.

Lack of sleep or decreased sleep quality may result in health problems, such as depression or anxiety. In order to improve the quality of sleep, sensors are typically used to detect brain wave activity of a person and to determine the stages of sleep the person cycles through. The person can then use such information to identify factors causing lower sleep quality and to modify his habits to improve sleep quality. However, attaching a sensor that detects brain waves is often difficult to maintain attached to the forehead because of the typical movement a person undergoes during sleep.

Figure 1:
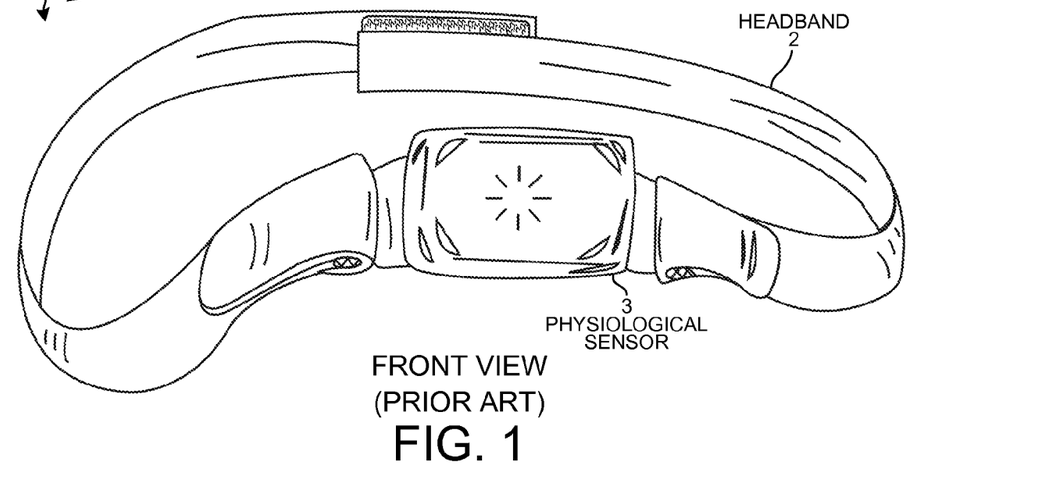
FIG. 1 (Prior Art) is a perspective diagram of a front view of a conventional physiological sensor apparatus for detecting brain wave activity of a user.
Figure 2:
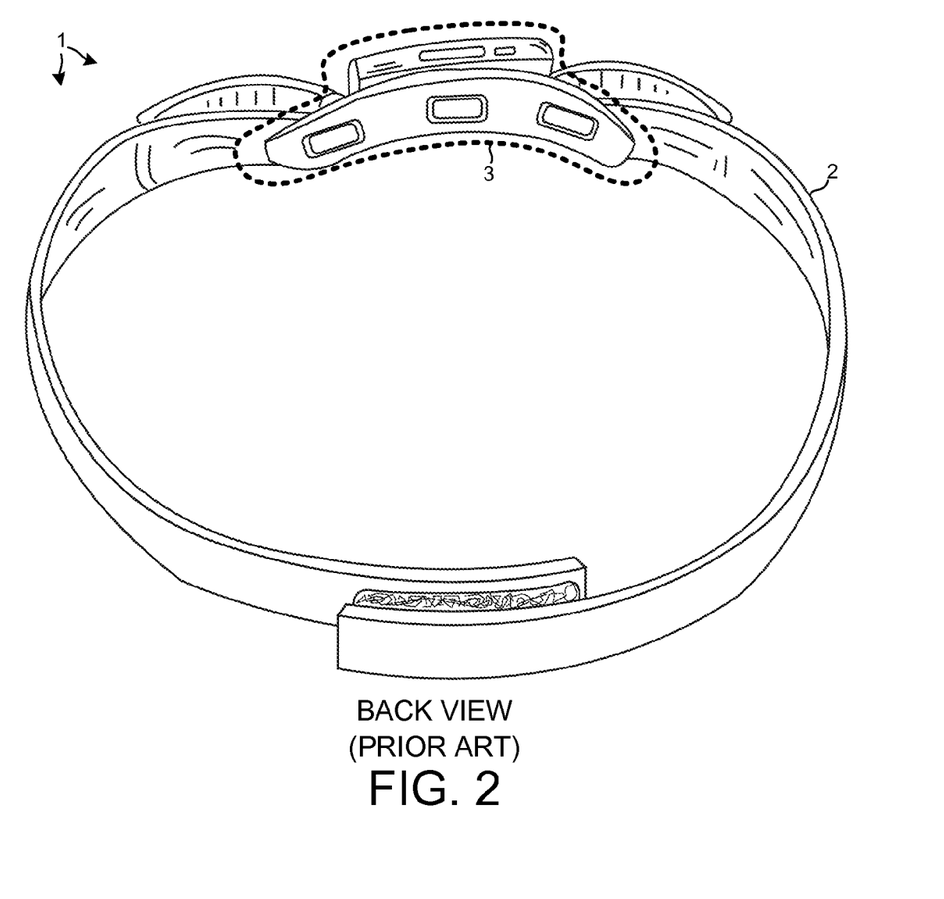
FIG. 2 (Prior Art) is a perspective diagram of a back view of the conventional physiological sensor apparatus.
Figure 3:
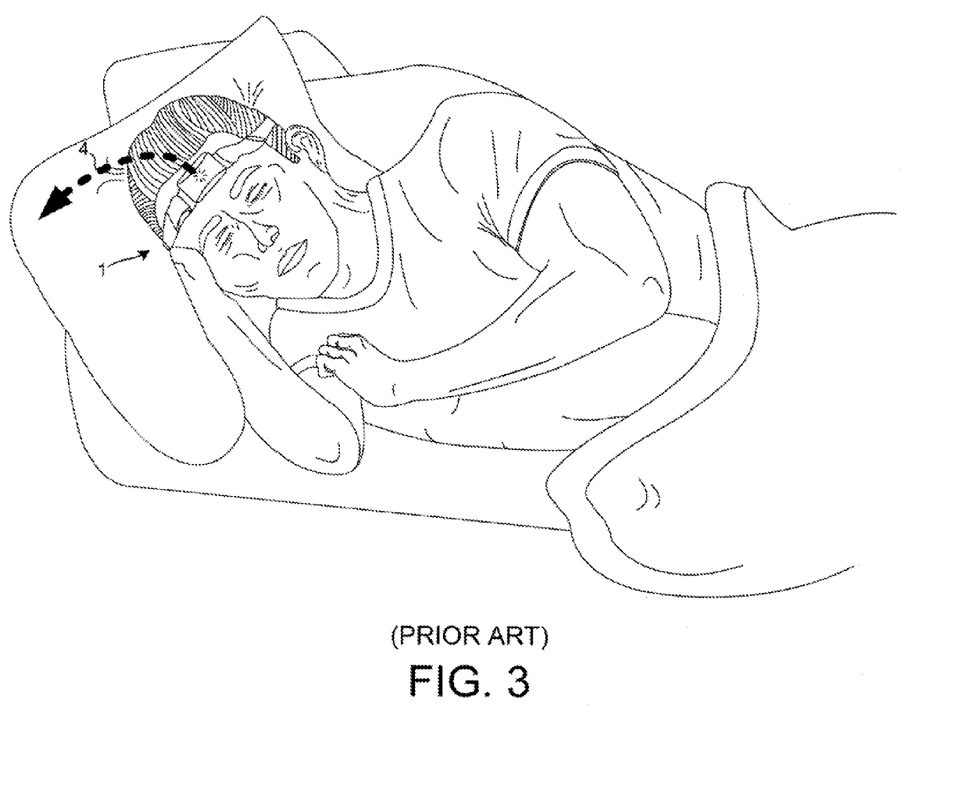
FIG. 3 (Prior Art) is a perspective diagram showing how the conventional physiological sensor apparatus is displaced from the user's forehead during a period of sleep.

FIG. 1 (Prior Art) is a perspective diagram of a front view of a conventional physiological sensor apparatus 1 for detecting brain wave activity of a user. The physiological sensor apparatus 1 uses a headband 2 to secure physiological sensor 3 to a forehead of the user. FIG. 2 (Prior Art) is a perspective diagram of a back view of the conventional physiological sensor apparatus 1. FIG. 3 (Prior Art) is a perspective diagram showing how the conventional physiological sensor apparatus 1 is displaced from the user's forehead during a period of sleep. Reference numeral 4 identifies a displacement of the sensor 2 away from the forehead due to a user moving during sleep. Because the sensor 2 often becomes displaced or removed during the night, the obtained brain wave activity information is often inaccurate or incomplete. A solution that overcomes these challenges is desired.

SUMMARY

A physiological sensor apparatus comprises a physiological sensor, a headband and an eye mask. The sensor senses a signal indicative of a sleep stage of a user. The sleep stage may be a rapid eye movement (REM) stage, a non-rapid eye movement (NREM) stage, or another type of sleep stage used to characterize the state of sleep of the user. The sensor is used to determine the various sleep stages exhibited by the user during a time period of sleep. In one example, the physiological sensor includes a plurality of Electroencephalography (EEG) electrodes configured to sense brain waves when the EEG electrodes are disposed on a forehead of the user.

The headband and eye mask are used to maintain the position of the sensor as it is disposed on the forehead of the user and prevent the electrodes from being displaced during the period of time. The headband is attached to the sensor and is adjustable to fit securely around a forehead of the user. The headband has a first end that attaches to a first clasp located at a first end of the sensor, and the headband has second end that attaches to a second clasp located at a second end of the sensor. A diameter of the headband is adjustable by the user to secure the sensor to the forehead of the user. The diameter is adjusted by adjusting a Velcro portion located at each end of the headband.

The eye mask has a first eye patch portion and a second eye patch portion. The first eye patch portion forms a first lateral edge and a first inner edge. A first attachment mechanism attaches the first lateral edge to the first end of the headband. The second eye patch portion forms a second lateral edge and a second inner edge. A second attachment mechanism attaches the second lateral edge to the second end of the headband. If the headband did not include the attached eye mask, then the sensor would shift away from the forehead due to movements that a typical user undergoes during sleep.

The first and second inner edges of the eye mask extend along a first axis and are adjacent to each other. The sensor extends from the first end of the headband to the second end of the headband along a second axis. The second axis is perpendicular to the first axis. As a result of this configuration, the eye mask is disposed over eyes of the user when the sensor is disposed on the forehead of the user.

A nasal edge is formed by the first eye patch portion and the second eye patch portion. The nasal edge is adapted to be disposed on a nose of the user when the sensor is disposed on a forehead of the user. The first axis bisects the nasal edge. The nasal edge provides additional support to secure the sensor to the forehead during sleep and to prevent the sensor from being displaced. In another embodiment, no nasal edge is present and the eye mask forms a convex shape. The sensor accurately determines the sleep stages of the user over a period of sleep of the user because the adjustable headband and eye mask prevent the electrodes from being displaced from the forehead of the user during the period of sleep.

In accordance with another novel aspect, the eye mask does not cover the user's eyes while the physiological sensor apparatus is being used. The user secures the physiological sensor apparatus in an upside-down orientation so that the eye mask is disposed above the user's forehead. In the upside-down orientation, the physiological sensor apparatus still functions to maintain the sensor against the user's forehead during sleep because the eye mask is supported against the upper forehead of the user. Although the nose is not used for support in this orientation, the contact between the mask and the upper forehead provides sufficient resistance to prevent the sensor from being displaced from the forehead during sleep.

In accordance with a second embodiment, a physiological sensor apparatus comprises a physiological sensor, a head cap, and adjustable straps. The sensor senses a signal indicative of a sleep stage of a user. In one example, the physiological sensor includes a plurality of Electroencephalography (EEG) electrodes configured to sense brain waves when the EEG electrodes are disposed on a forehead of the user. The head cap and the adjustable straps are used to maintain the position of the sensor as it is disposed on the forehead of the user and prevent the electrodes from being displaced during the period of time. The head cap is attached to the sensor via the adjustable straps. A diameter of the apparatus is adjustable by the user to secure the sensor to the forehead of the user. If the apparatus did not include the headband, then the sensor would shift away from the forehead due to movements that a typical user undergoes during sleep.

Further details and embodiments and techniques are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

DETAILED DESCRIPTION

Reference will now be made in detail to background examples and some embodiments of the invention, examples of which are illustrated in the accompanying drawings.

Figure 4:
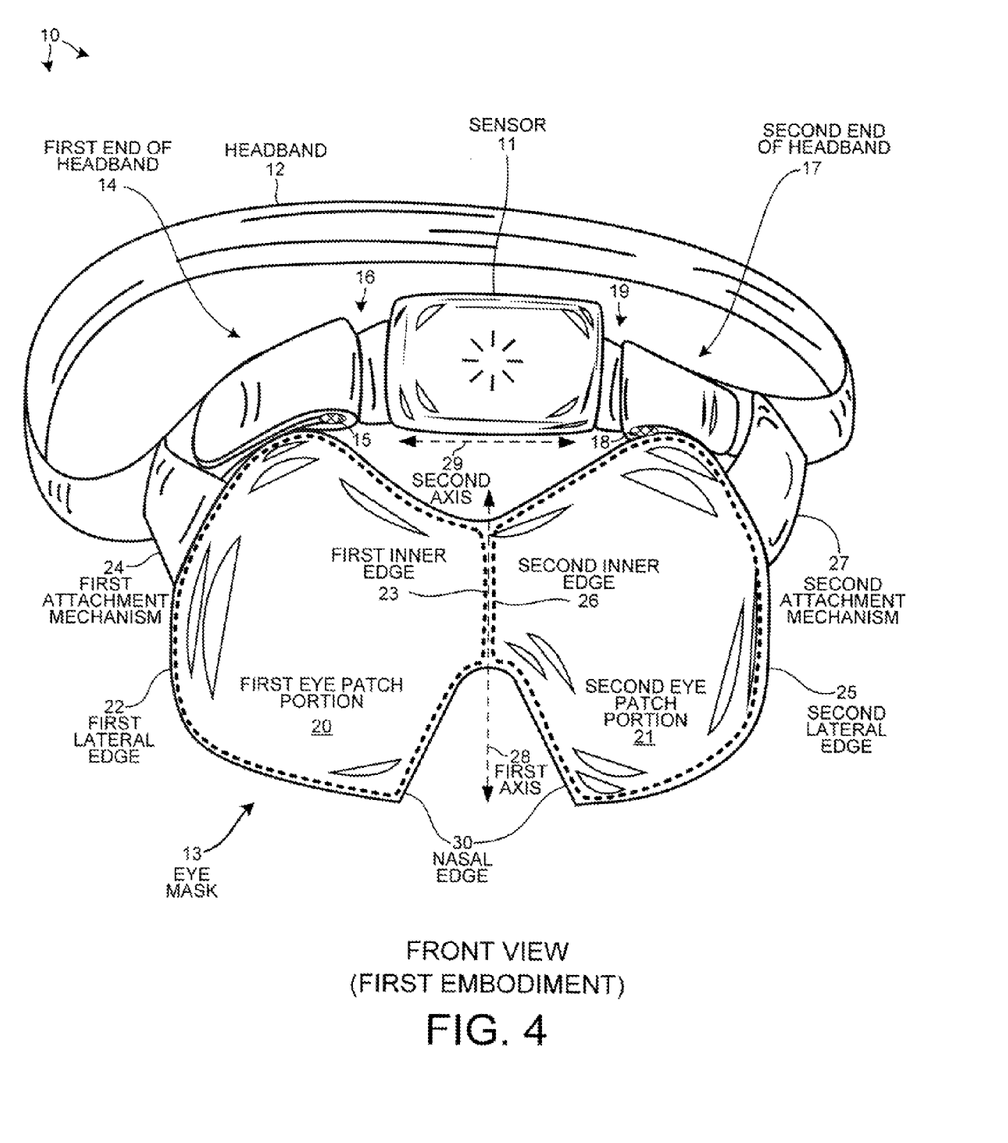
FIG. 4 is a perspective diagram of a front view of a first embodiment of a physiological sensor apparatus.

FIG. 4 is a perspective diagram of a front view of a physiological sensor apparatus 10, in accordance with a first embodiment. The physiological sensor apparatus 10 includes a sensor 11, a headband 12, and an eye mask 13. When the physiological sensor apparatus 10 is worn by a user during sleep, the sensor 11 senses a signal indicative of a sleep stage of the user. The sleep stage of the user detected by the sensor 11 may be a rapid eye movement (REM) stage, a non-rapid eye movement (NREM) stage, or another sleep stage used to characterize the state of sleep of the user.

The headband is attached to the sensor and is adjustable to fit securely around a forehead of the user. The headband 12 has first end 14 that attaches to a clasp 15 of the sensor 11. The first clasp 15 of the sensor 11 is located at a first end 16 of the sensor 11. Similarly, the headband 12 has second end 17 that attaches to a clasp 18 of the sensor 11. The second clasp 18 of the sensor 11 is located at a second end 19 of the sensor 11.

The eye mask 13 is used to secure the sensor 11 to the forehead of the user while the user sleeps. The eye mask 13 includes a first eye patch portion 20 and a second eye patch portion 21. The first eye patch portion 20 has a first lateral edge 22 and a first inner edge 23. A first attachment mechanism 24 attaches the first lateral edge 22 of the first eye patch portion 20 to the first end 14 of the headband 12. Similarly, the second eye patch portion 21 forms a second lateral edge 25 and a second inner edge 26. A second attachment mechanism 27 attaches the second lateral edge 25 of the second eye patch portion 21 to the second end 17 of the headband 12. Accordingly, the first eye patch portion 20 is attached to the first end 14 of the headband 12, and the second eye patch portion 21 is attached to the second end 17 of the headband 12.

Reference numeral 28 identifies a first axis. The first inner edge 23 extends along the first axis 28, and the second inner edge 26 also extends along the first axis 28. Thus, the first inner edge 23 is adjacent to the second inner edge 26. In this embodiment, the eye patch portion 20 and the second eye patch portion 21 form a single unitary structure. In another embodiment, an elastic attachment portion attaches the first eye patch portion 20 to the second eye patch portion 21.

Reference numeral 29 identifies a second axis. The sensor 11 extends from the first end 14 of the headband 12 to the second end 17 of the headband 12 along the second axis 29. The second axis 29 is perpendicular to the first axis 28. As a result of this configuration, the eye mask 13 is disposed over eyes of a user when the sensor 11 is disposed on the forehead of the user. If the eye mask 13 were not present, then the sensor 11 would shift away from the forehead due to movements a typical user experiences during sleep. Furthermore, the sensor 11 would not accurately sense sleep stages of the user because the sensor 11 obtains the most accurate measurements when in contact with the forehead of the user.

The first eye patch portion 20 and the second eye patch portion 21 have nasal edges 30. The nasal edge 30 is adapted to be disposed on a nose of the user when the sensor 11 is disposed on a forehead of the user. The first axis 28 bisects the nasal edge 30. The nasal edge 30 provides additional support to secure the sensor 11 to the forehead during sleep and to prevent the sensor 11 from shifting. In another embodiment, no nasal edge is present and the eye mask forms a convex shape.

In addition to providing stability, each of the first and second eye patch portions 20, 21 is opaque such that no amount of visible light passes through the eye patch portion. As such, the eye mask 13 also provides the user with extra comfort during sleep. In another embodiment, the eye mask 13 is infused with a scent, such as a green tea infused scent, to provide additional sleep-related advantages.

Figure 5:
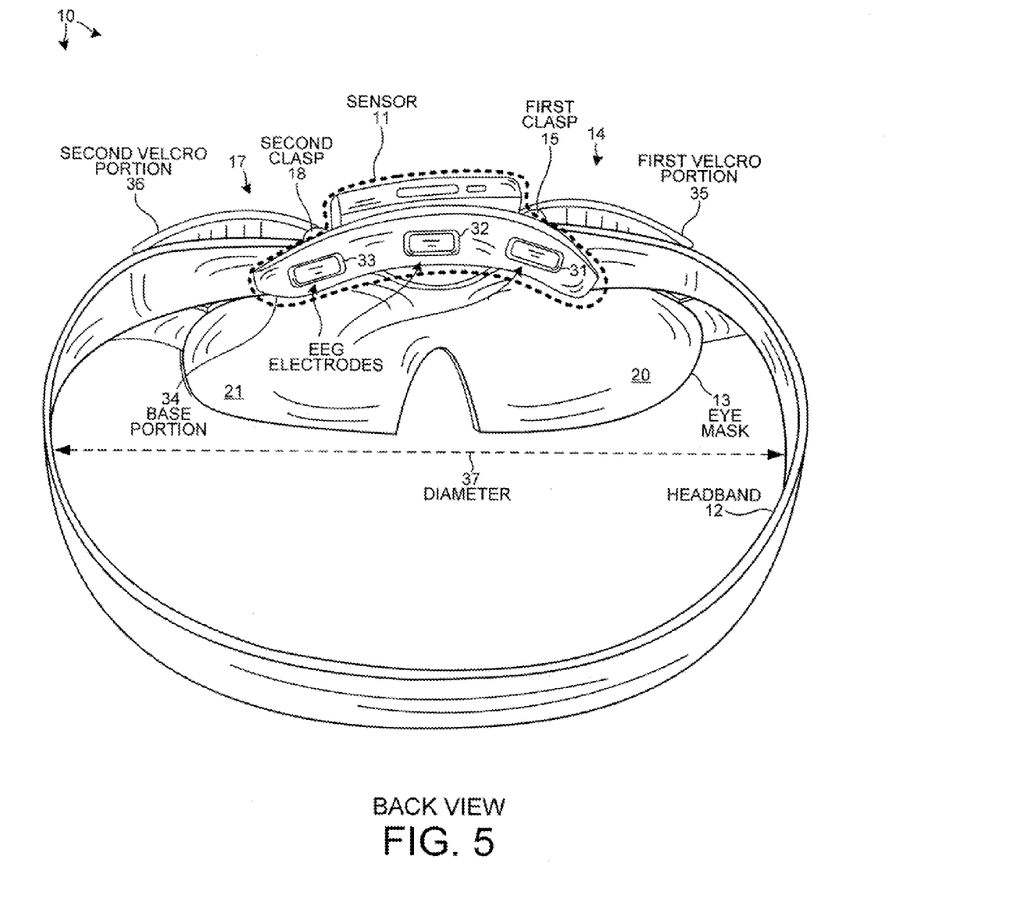
FIG. 5 is a perspective diagram of a back view of the physiological sensor apparatus.

FIG. 5 is a perspective diagram of a back view of the physiological sensor apparatus 10. The sensor 11 comprises a plurality of electroencephalography (EEG) electrodes 31-33 and a base portion 34. Each of the EEG electrodes 31-33 is disposed on the base portion 34. The signal indicative of the sleep stage of the user is an EEG signal that is detected using the EEG electrodes 31-33 and circuitry (not shown) contained in base portion 34. For additional information on the structure and operation of sensor 11, see: 1) U.S. patent publication number 2010/0099954, entitled "Data-Driven Sleep Coaching System", filed on May 6, 2009, by Dickinson et al.; and 2) U.S. patent publication number 2013/0060097, entitled "Multi-Modal Sleep System", filed on Sep. 6, 2011, by Rubin et al. (the entire subject matter of each of these patent documents is incorporated herein by reference).

The headband 12 and eye mask 13 are adjustable to fit securely on the user. The first end 14 of headband 12 includes a first Velcro portion 35 that extends through the first clasp 15. The second end 17 of headband 12 includes a second Velcro portion 36 that extends through the second clasp 18. The user is able to adjust a diameter 37 of the headband 12 to fit securely around the head of the user by adjusting how the first and second Velcro portions 35, 36 extend through the first and second clasps 15, 18.

Figure 6:
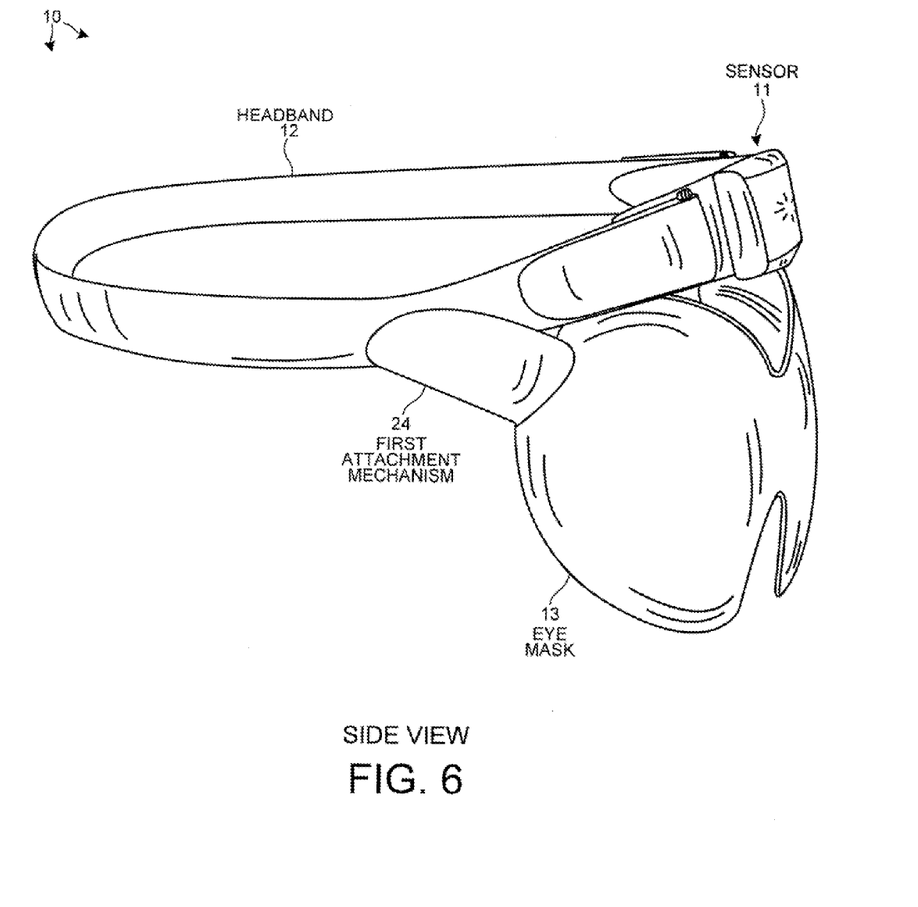
FIG. 6 is a perspective diagram of a side view of the physiological sensor apparatus.

FIG. 6 is a perspective diagram of a side view of the physiological sensor apparatus 10.

Figure 7:
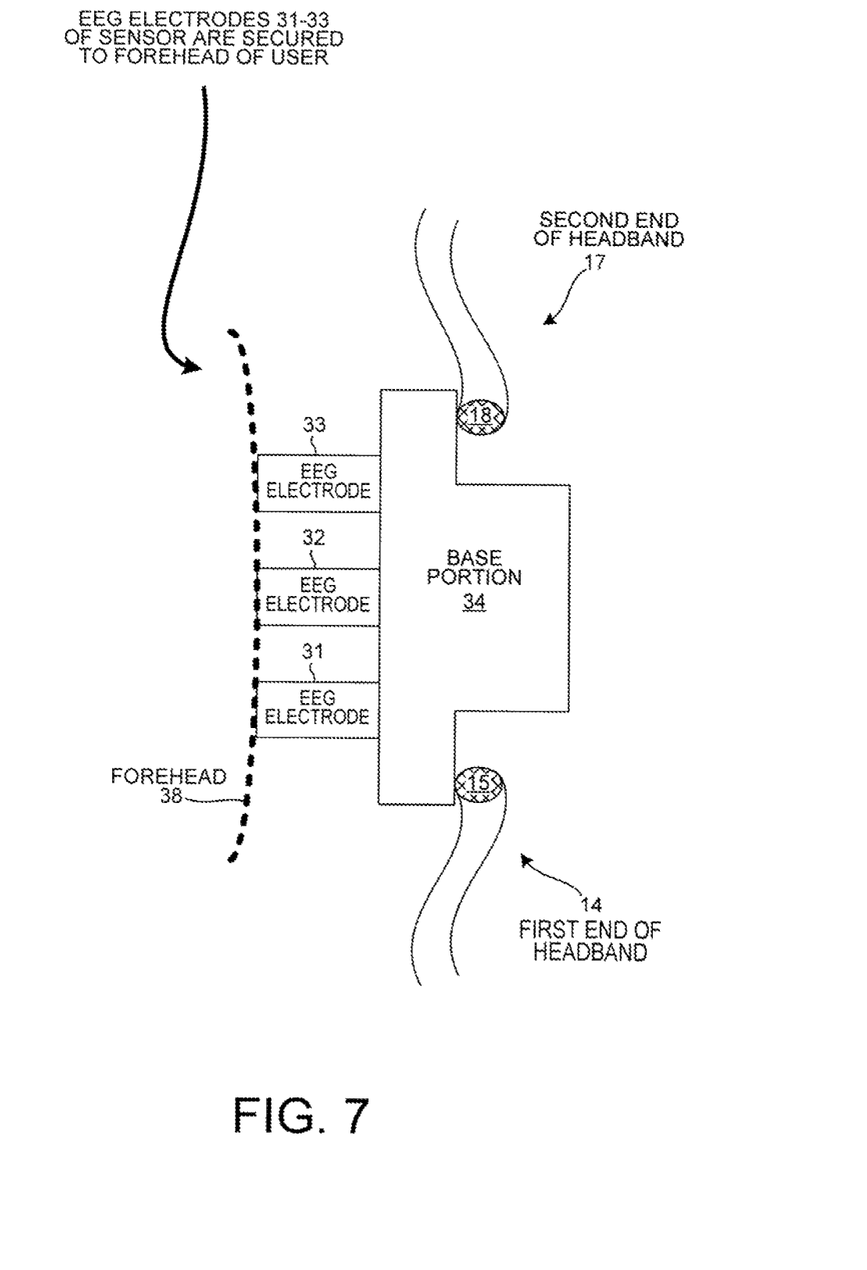
FIG. 7 is a diagram showing how the EEG electrodes 31-33 are disposed on the forehead of the user.

FIG. 7 is a diagram showing how the EEG electrodes 31-33 are disposed on the forehead of the user. Reference numeral 38 identifies a dashed line representing the forehead of the user. The sensor detects a signal indicative of a sleep stage using the EEG electrodes 31-33 and circuitry contained in the base portion 34.

Figure 8:
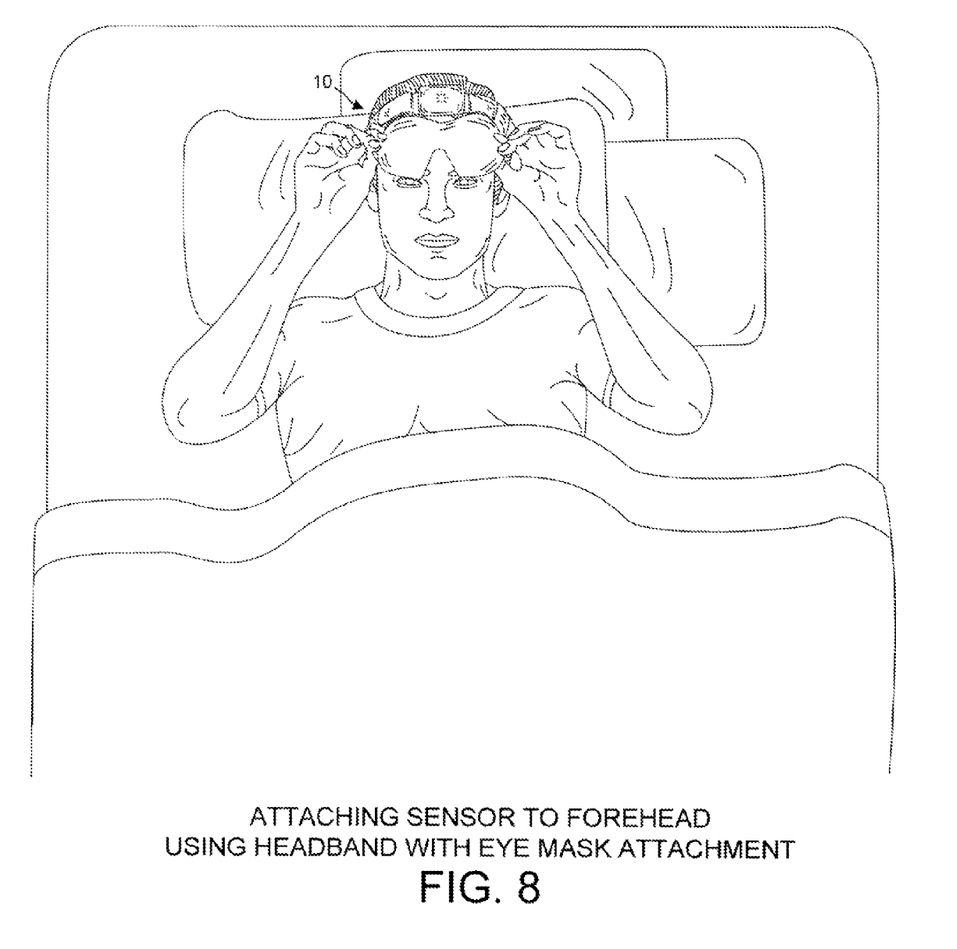
FIG. 8 is a perspective diagram showing how the physiological sensor apparatus is secured to the forehead of the user.

FIG. 8 is a perspective diagram showing how the headband 12 and attached eye mask 13 are used to secure the sensor 11 to the forehead of the user. The user pulls apparatus 10 down over his head such that electrodes 31-33 contact the user's forehead, and eye mask 13 covers the user's eyes. The fit of the eye mask 13 over the user's nose and eyes helps secure the sensor 11 to the user's forehead even when the user rolls over onto his side or stomach.

Figure 9:
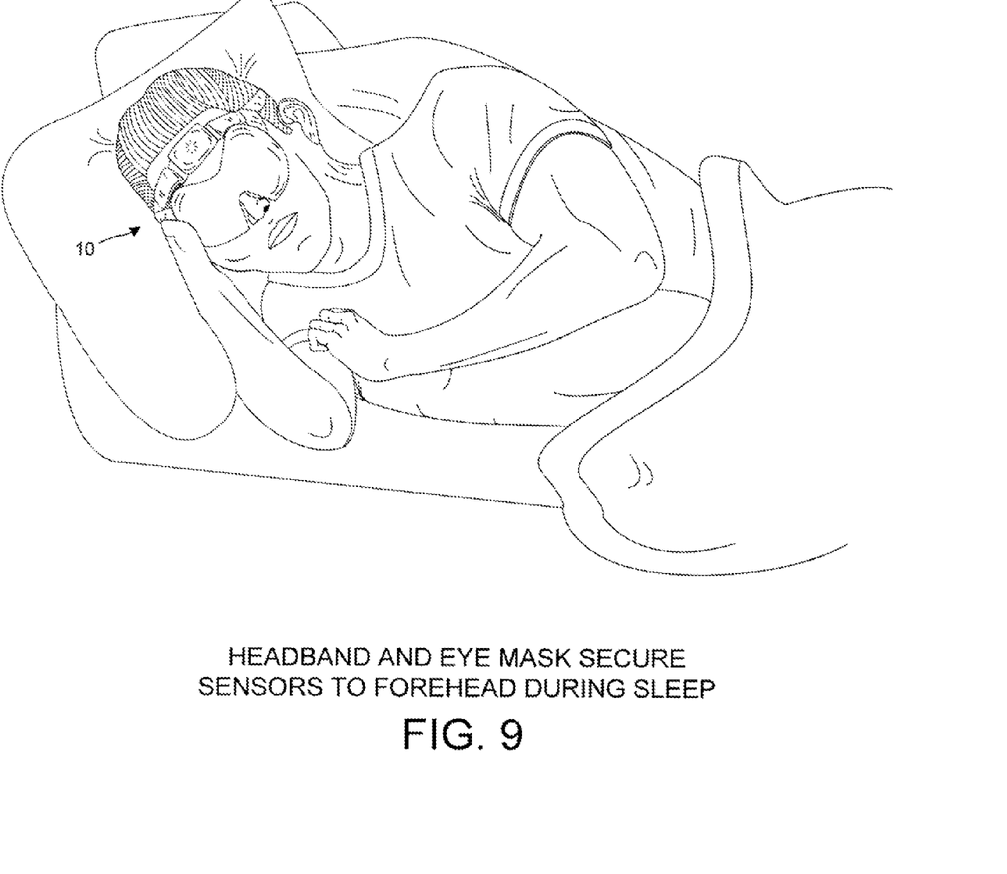
FIG. 9 is a perspective diagram showing how the physiological sensor apparatus fits securely on the user during a period of sleep.

FIG. 9 is a perspective diagram showing how the physiological sensor apparatus 10 fits securely on the user during a time period of sleep. As a result of using the physiological sensor apparatus 10 to attach the sensor 11 to the forehead, no additional sensor is needed to accurately determine the sleep stage of the user. Accordingly, the physiological sensor apparatus 10 detects the sleep stage of the user using one and only one sensor, and without using other additional physiological sensors attached to other parts of the body. FIG. 9 shows that sensor 11 is secured to the user's forehead even when the user has rolled over onto his side.

Figure 10:
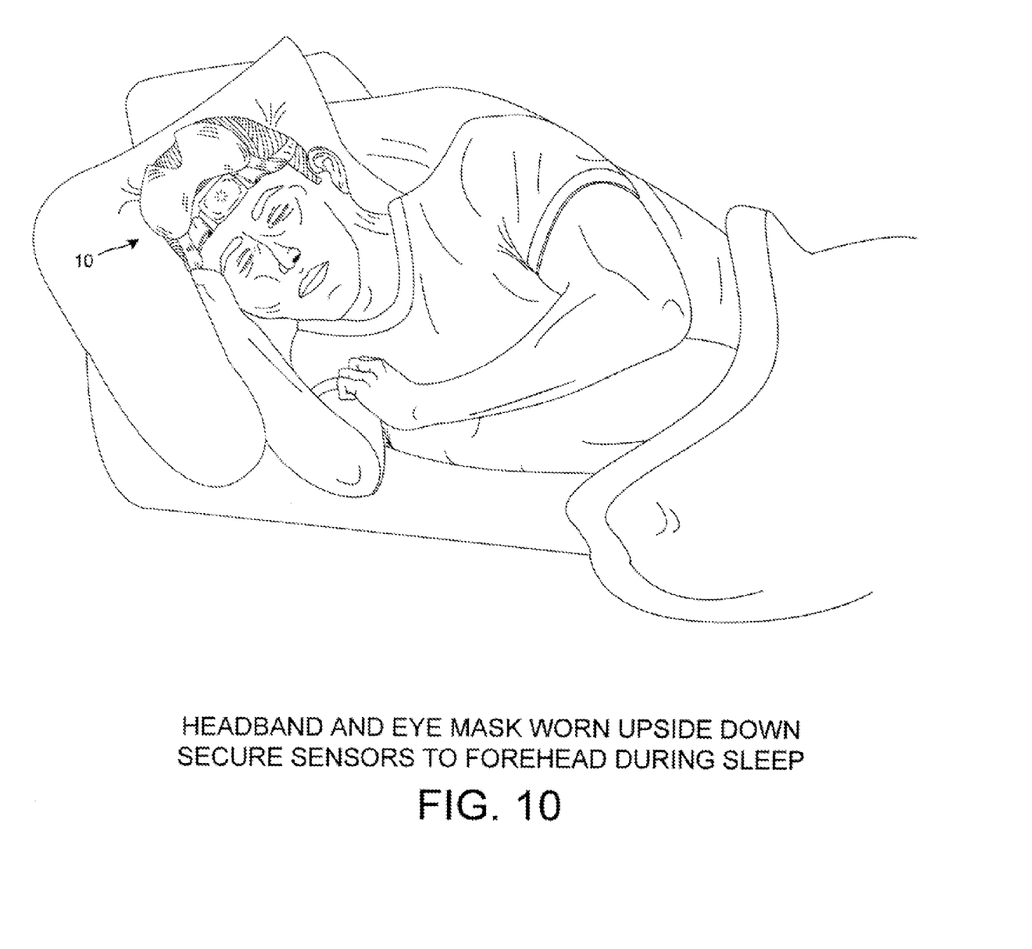
FIG. 10 is a perspective diagram showing how the physiological sensor apparatus fits securely on the user in an upside-down orientation so that the user's eyes remain uncovered during the period of sleep.

FIG. 10 is a perspective diagram showing how the physiological sensor apparatus 10 can be secured on the user in an upside-down orientation during a time period of sleep. In accordance with another novel aspect, if the user prefers not to utilize the eye mask 13 to cover his eyes during sleep, then the user may still attach the sensor 11 to the forehead by wearing the physiological sensor apparatus 10 upside-down so that his eyes remain uncovered. Although the nose is not used for support in the upside-down orientation, the contact between the mask and the upper forehead provides sufficient resistance to prevent the sensor from being displaced from the forehead during sleep. Accordingly, the physiological sensor apparatus still functions to maintain the sensor against the user's forehead during sleep.

Figure 11:
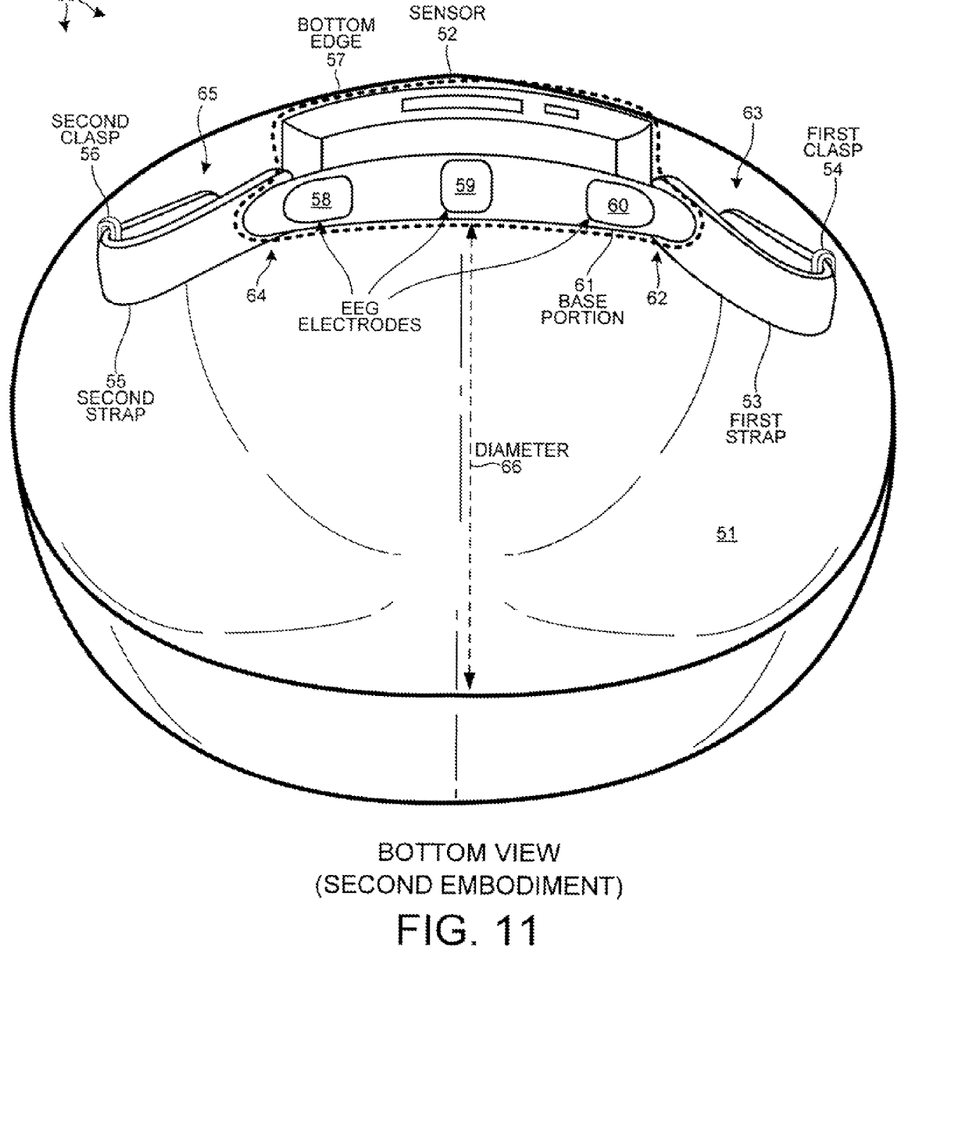
FIG. 11 is a perspective diagram of a bottom view of a second embodiment of a physiological sensor apparatus.

FIG. 11 is a perspective diagram of a bottom view of a physiological sensor apparatus 50, in accordance with a second embodiment. FIG. 11 shows a physiological sensor attached inside a sleeping cap 51. The physiological sensor apparatus 50 includes head cap 51, a physiological sensor 52, a first strap portion 53, a first clasp 54, a second strap portion 55, and a second clasp 56. The sensor 52 is disposed on the inside along a bottom edge 57 of the head cap 51.

The physiological sensor 52 comprises a plurality of electroencephalography (EEG) electrodes 58-60 and a base portion 61. Each of the EEG electrodes 58-60 is disposed on the base portion 61. The signal indicative of the sleep stage of the user is an EEG signal that is detected using the EEG electrodes 58-60 and circuitry (not shown) contained in base portion 61. The sensor 52 is of similar construction and operates in a similar fashion as the sensor 11 of FIG. 5.

The head cap 51, first strap portion 53 and second strap portion 55 are used to secure the sensor 52 to the forehead of the user while the user sleeps. A first end 62 of the first strap portion 53 is attached to an end of the sensor 52, and a second end 63 of the first strap portion 53 extends through first clasp 54 and attaches to the first strap portion 53 via a Velcro attachment. A first end 64 of the second strap portion 55 is attached to an opposite end of the sensor 52, and a second end 65 of the second strap portion 55 extends through second clasp 56 and attaches to the second strap portion 55 via a Velcro® attachment. A diameter 66 of the apparatus 50 is adjustable by the user to secure the sensor 52 to the forehead of the user. The user secures the sensor 52 by adjusting the strap portions 53 and 55 to tighten or loosen the strap portions 53 and 55 against the user's forehead.

Figure 12:
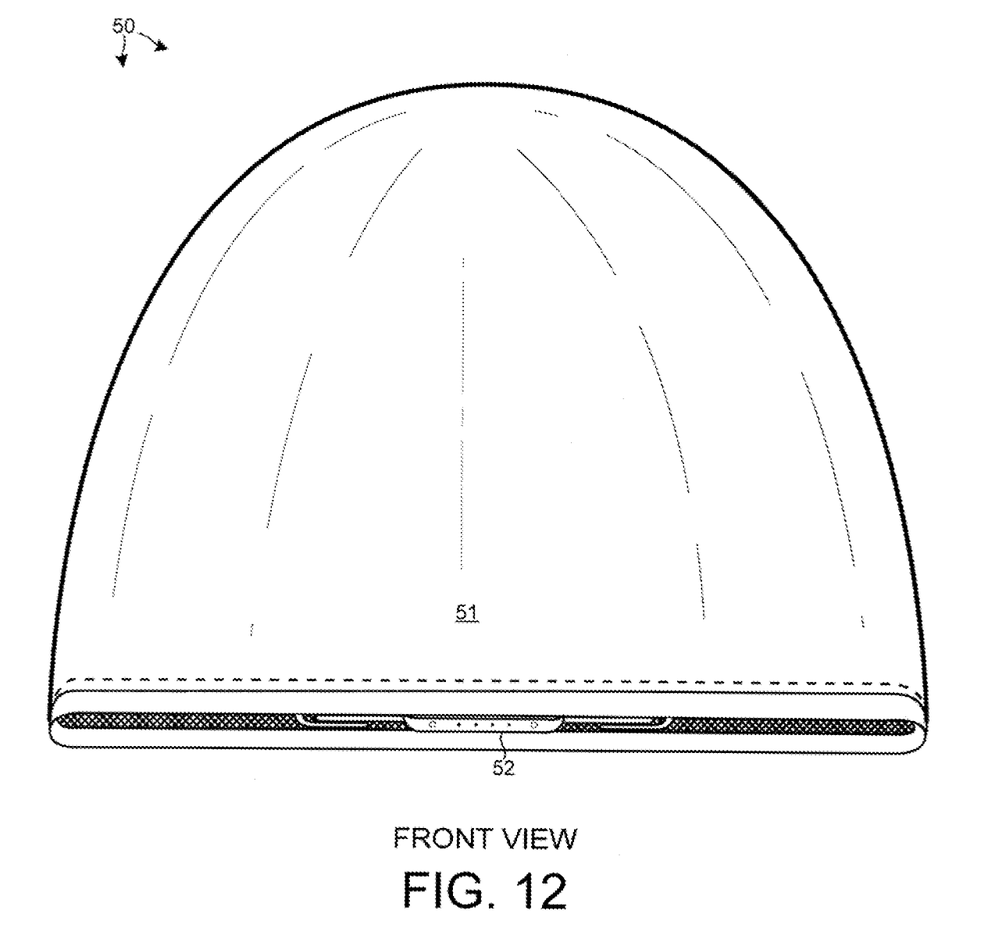
FIG. 12 is a perspective diagram of a front view of the physiological sensor apparatus.

FIG. 12 is a perspective diagram of a front view from outside cap 51 of the physiological sensor apparatus 50.

Figure 13:
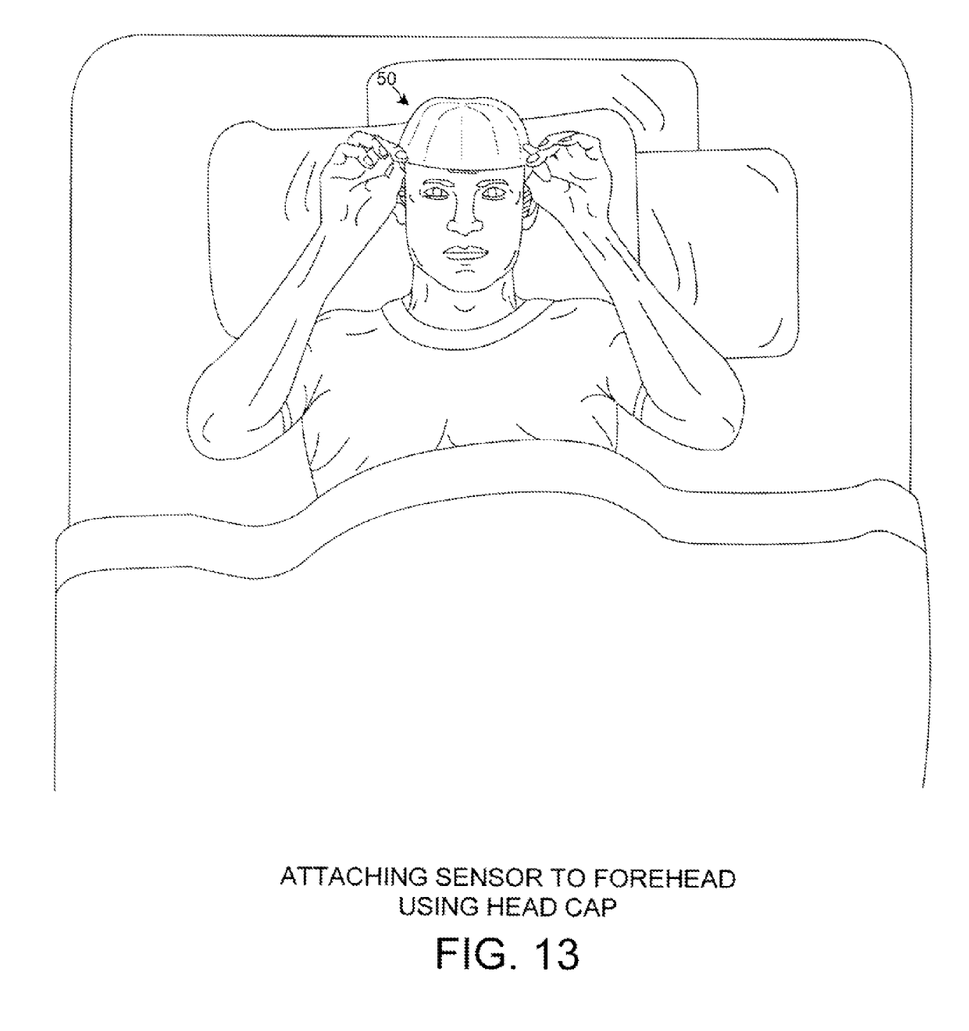
FIG. 13 is a perspective diagram showing how the physiological sensor apparatus is secured to the forehead of the user.

FIG. 13 is a perspective diagram showing how the physiological sensor apparatus 50 is secured to the forehead of the user. The user pulls apparatus 50 down over his head such that electrodes 58-60 contact the user's forehead, and head cap 51 covers the user's head. The fit of the head cap 51 over the user's head helps secure the sensor 52 to the user's forehead even when the user rolls over onto his side or stomach.

Figure 14:
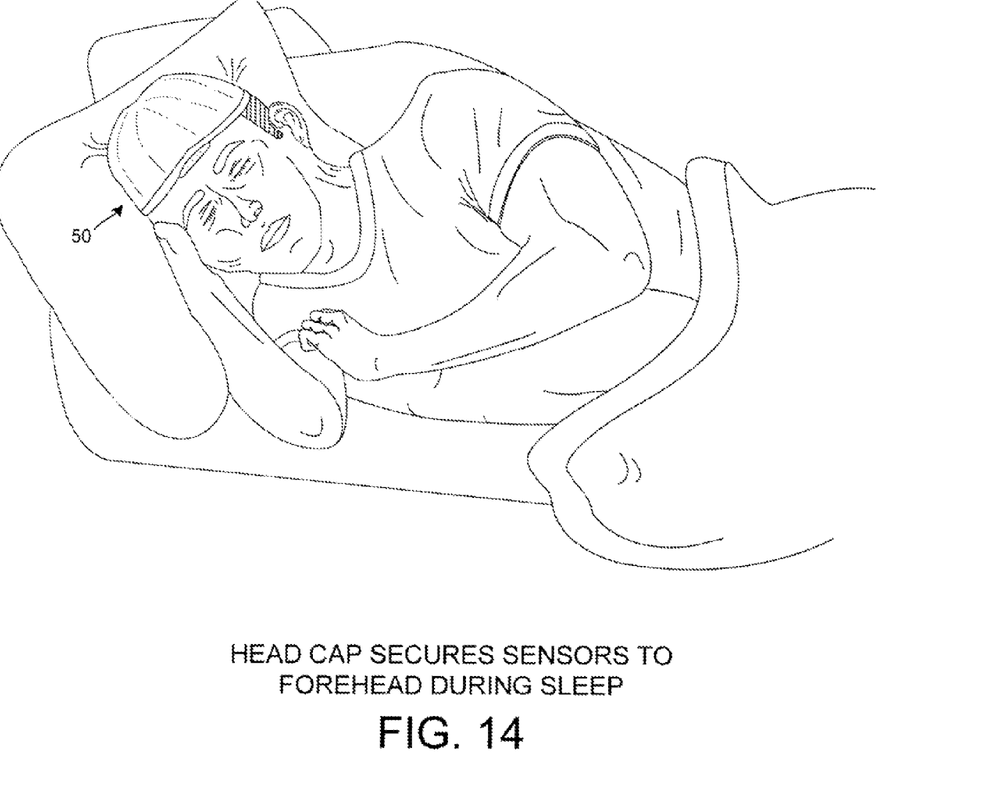
FIG. 14 is a perspective diagram showing how the physiological sensor apparatus fits securely on the user during a period of sleep.

FIG. 14 is a perspective diagram showing how the physiological sensor apparatus 50 fits securely on the user during a time period of sleep. As a result of using the physiological sensor apparatus 50 to attach the sensor 52 to the forehead, no additional sensor is needed to accurately determine the sleep stage of the user. Accordingly, the physiological sensor apparatus 50 detects the sleep stage of the user using one and only one sensor, and without using other additional physiological sensors attached to other parts of the body. FIG. 14 shows that sensor 52 is secured to the user's forehead even when the user has rolled over onto his side.

Figure 15:
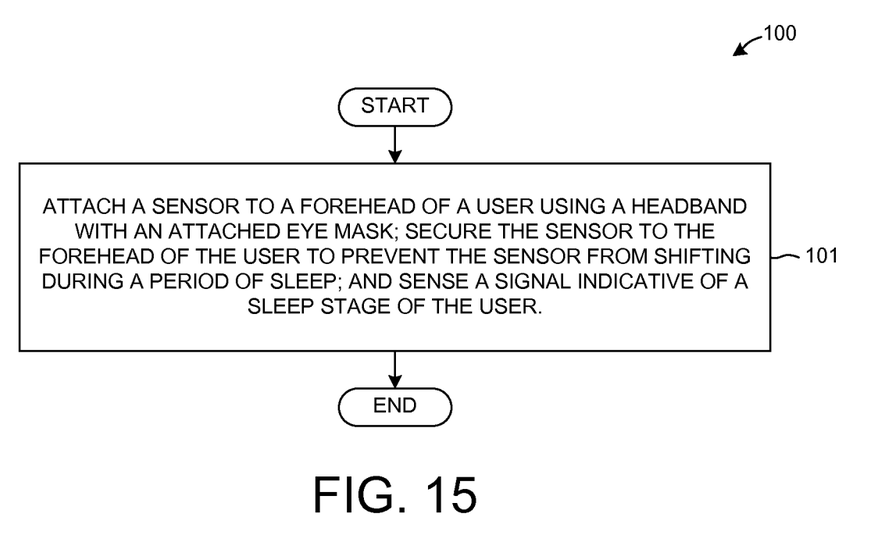
FIG. 15 is a flowchart of a method in accordance with another novel aspect.

FIG. 15 is a flowchart 100 of a method in accordance with another novel aspect. In a first step (step 101), a sensor is attached to a forehead of a user using a headband with an attached eye mask. For example, as shown in FIG. 8, the sensor 11 is attached to the forehead of the user using the headband 12 and attached eye mask 13. The sensor is disposed on the forehead in a secure fashion and does not shift during a period of sleep of the user.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. An apparatus comprising:
   a sensor that senses a signal indicative of a sleep stage of a user, wherein the sensor determines the sleep stage of the user from the sensed signal, and wherein the sensor has a first end and a second end;
   a headband having a first end and a second end, wherein the first end of the headband attaches to the first end of the sensor, and wherein the second end of the headband attaches to the second end of the sensor;
   an eye mask that comprises a first eye patch portion and a second eye patch portion, wherein the first eye patch portion forms a first lateral edge, and wherein the second eye patch portion forms a second lateral edge;

a first attachment mechanism, wherein the first attachment mechanism attaches the first lateral edge of the first eye patch portion to the first end of the headband; and a second attachment mechanism, wherein the second attachment mechanism attaches the second lateral edge of the second eye patch portion to the second end of the headband.

2. The apparatus of claim 1, wherein the first eye patch portion forms a first inner edge, wherein the second eye patch portion forms a second inner edge, and wherein the first inner edge is adjacent to the second inner edge.

3. The apparatus of claim 2, wherein the first inner edge extends along a first axis and the second inner edge extends along the first axis, wherein the sensor extends from the first end of the headband to the second end of the headband along a second axis, and wherein the second axis is perpendicular to the first axis.

4. The apparatus of claim 1, wherein each of the first and second eye patch portions is opaque such that no amount of visible light passes through the eye patch portion.

5. The apparatus of claim 1, wherein the eye mask is a single unitary structure.

6. The apparatus of claim 1, wherein the first eye patch portion and the second eye patch portion form a nasal edge, wherein the nasal edge is adapted to be disposed on a nose of the user when then the sensor is disposed on a forehead of the user.

7. The apparatus of claim 1, wherein the sensor includes a first clasp and a second clasp, wherein the first clasp is at the first end of the sensor and the second clasp is at the second end of the sensor, and wherein the first end of the headband attaches to the first clasp and the second end of the headband attaches to the second clasp such that a diameter of the headband is adjustable.

8. The apparatus of claim 1, wherein the sleep stage of the user is determined during a period of time using only the sensor, wherein no other sensor is used to determine the sleep stage of the user during the period of time, and wherein the sleep stage of the user is selected from the group consisting of: a rapid eye movement (REM) stage, and a non-rapid eye movement (NREM) stage.

9. The apparatus of claim 1, wherein the sensor comprises a base portion and an Electroencephalography (EEG) electrode, wherein the EEG electrode is disposed on the base portion, and wherein the signal indicative of the sleep stage of the user is an EEG signal detected using the EEG electrode.

10. The apparatus of claim 1, wherein the first eye patch portion is attached to the second eye patch portion via an elastic attachment portion.

11. The apparatus of claim 1, wherein the eye mask is infused with a scent.

12. A method comprising:

attaching a sensor that includes Electroencephalography (EEG) electrodes to a forehead of a user using a headband with an attached eye mask, wherein the sensor is adapted to determine a sleep stage of the user from brain waves sensed by the EEG electrodes disposed on the forehead of the user, wherein the headband has a first end that attaches to a first end of the sensor and a second end that attaches to a second end of the sensor, and wherein the eye mask comprises a first eye patch portion that is attached to the first end of the headband via a first attachment mechanism and a second eye patch portion that is attached to the second end of the headband via a second attachment mechanism.

13. The method of claim 12, wherein the first eye patch portion and the second eye patch portion form a nasal edge, wherein the nasal edge is disposed on a nose of the user and the sensor is disposed on a forehead of the user as a result of the attaching.

14. The method of claim 12, further comprising:

adjusting a diameter of the headband to fit securely on the forehead of the user, wherein the sensor includes a first clasp and a second clasp, wherein the first clasp is at the first end of the sensor and the second clasp is at the second end of the sensor, and wherein the first end of the headband attaches to the first clasp and the second end of the headband attaches to the second clasp such that the diameter of the headband is adjustable.

15. The method of claim 12, wherein the first eye patch portion forms a first lateral edge and a first inner edge, wherein the second eye patch portion forms a second lateral edge and a second inner edge, and wherein the first inner edge is adjacent to the second inner edge.

16. The method of claim 15, wherein the first inner edge extends along a first axis and the second inner edge extends along the first axis, wherein the sensor extends from the first end of the headband to the second end of the headband along a second axis, and wherein the second axis is perpendicular to the first axis.

17. The method of claim 15, wherein the first attachment mechanism attaches the first lateral edge of the first eye patch portion to the first end of the headband, and wherein the second attachment mechanism attaches the second lateral edge of the second eye patch portion to the second end of the headband.

18. The method of claim 12, wherein the sleep stage of the user is determined during a period of time during which the sensor is the only sensor used to determine the sleep stage of the user, and wherein the sleep stage of the user is taken from the group consisting of: a rapid eye movement (REM) stage and a non-rapid eye movement (NREM) stage.

19. An apparatus comprising:

a sensor that senses a signal indicative of a sleep stage of a user, wherein the sensor has a first end and a second end;

a headband having a first end and a second end, wherein the first end of the headband attaches to the first end of the sensor, and wherein the second end of the headband attaches to the second end of the sensor;

a first attachment mechanism;

a second attachment mechanism; and an eye mask that comprises a first eye patch portion and a second eye patch portion, wherein the first eye patch portion is attached to the first end of the headband via the first attachment mechanism and the second eye patch portion is attached to the second end of the headband via the second attachment mechanism such that an open area is formed between a bottom edge of the sensor and an upper edge of the eye mask.

20. The apparatus of claim 19, wherein the first eye patch portion and the second eye patch portion form a nasal edge, wherein the nasal edge is adapted to be disposed on a nose of the user when then the sensor is disposed on a forehead of the user such that a portion of the forehead is exposed through the open area formed between the bottom edge of the sensor and the upper edge of the eye mask.

* * * * *